(12) United States Patent
Chinn

(10) Patent No.: US 6,473,654 B1
(45) Date of Patent: Oct. 29, 2002

(54) LEAD ANCHOR

(75) Inventor: Kenny Kinyen Chinn, Rosemead, CA (US)

(73) Assignee: Advanced Bionics Corporation, Sylmar, CA (US)

( * ) Notice: Subject to any disclaimer, the term of this patent is extended or adjusted under 35 U.S.C. 154(b) by 61 days.

(21) Appl. No.: 09/642,978

(22) Filed: Aug. 18, 2000

Related U.S. Application Data
(60) Provisional application No. 60/187,674, filed on Mar. 8, 2000.

(51) Int. Cl.[7] ................................................. A61N 1/05
(52) U.S. Cl. ......................... 607/126; 600/375; 604/175
(58) Field of Search .................................. 604/171, 174, 604/175, 178; 128/DIG. 26; 607/115–117, 119, 122–123, 126, 132; 600/372–375, 377, 381

(56) References Cited

U.S. PATENT DOCUMENTS

| | | | |
|---|---|---|---|
| 4,419,819 A | 12/1983 | Dickhudt et al. .............. 29/857 |
| 5,036,862 A | 8/1991 | Pohndorf ..................... 128/784 |
| 5,464,446 A | 11/1995 | Dreessen et al. ........... 607/116 |
| 5,476,493 A | * 12/1995 | Muff .......................... 604/175 |
| 5,603,730 A | * 2/1997 | Romkee ...................... 604/175 |
| 5,746,722 A | * 5/1998 | Pohndorf et al. ........... 604/175 |
| 5,843,146 A | 12/1998 | Cross, Jr. ..................... 607/115 |

* cited by examiner

*Primary Examiner*—Kennedy Schaetzle
*Assistant Examiner*—Kristen Droesch
(74) *Attorney, Agent, or Firm*—Laura Haburay Bishop; Bryant R. Gold

(57) ABSTRACT

An anchor is provided for securing an elongated cylindrical member, such as a lead cable, to surrounding tissue. The anchor has a simple design that allows the anchor to be held in place on, e.g., a lead cable, without the need for sutures. In addition, the anchor may be manipulated to allow the anchor to move along the cylindrical member. Manipulation of the anchor is straight-forward, simple, and does not require tools, yet the anchor is reliably held in place, requiring intentional manipulation to be released. The anchor includes two coaxial sleeves holding the ends of a coaxial spring. As one sleeve is rotated in relation to the other, the spring is twisted, causing the inner diameter of the spring to increase or decrease. Once the inner diameter of the spring is increased to the point that is becomes larger than the outer diameter of the cylindrical member it surrounds, the anchor can slide on the cylindrical member. By decreasing the inner diameter of the spring, the spring can grip the cylindrical member, thus securing the anchor in place on the cylindrical member. The anchor includes a locking mechanism for holding the sleeves, and thus the spring, in a certain position or positions.

28 Claims, 7 Drawing Sheets

LEAD ANCHOR

This application claims the benefit of provisional application No. 60/187,674, filed Mar. 8, 2000.

FIELD OF THE INVENTION

The present invention generally relates to an implantable tube or cable, such as a lead cable, for use with a medical device, and more particularly relates to an anchor for securing the tube or cable to the surrounding tissue.

BACKGROUND OF THE INVENTION

A variety of devices exist which make use of cables or tubes for delivering electrical signals, fluids, etc. from a medical device to a region of the body, or simply for holding device(s) in place. For example, electrical lead cables, i.e., leads or lead extensions, that detachably connect to an electrical device or to other lead cables may deliver electrical stimulation to a nerve, muscle, or other tissue. For instance, numerous medical devices, such as neural stimulation devices, cardiac pacemakers, and defibrillators, commonly establish a connection between an implanted lead or lead extension (both will be referred to herein as lead cables or simply leads) and an implanted electronic package. In a typical pacemaker, the proximal end of a lead may be removably connected to a lead extension, which in turn is removably connected to an implantable pulse generator. The distal end of the lead, containing one or more electrodes, is typically inserted in or on the heart.

The most effective position of the electrodes or other devices at and/or along the distal end of the lead is commonly determined during surgery. Once the lead is implanted in this preferred position, it needs to be secured to surrounding tissue to prevent it from becoming dislodged. Accordingly, a lead anchor (also referred to as a suture sleeve) that surrounds or is a part of a lead cable may be provided. The lead anchor may require the physician to use, for instance, suture material to secure the anchor to the lead cable. Generally, lead anchors are configured to allow a physician to wrap suture(s) around and/or through the lead anchor multiple times, while securing the sutures to the adjacent tissue.

While securing the lead anchor to the lead cable and while securing the anchor (and thus the lead) to the adjacent tissue, a common problem is over-tightening of the sutures. The stresses resulting from over-tightening can damage the wires within the lead cable and/or break the insulation, which may ultimately cause the lead to fail. Thus, the lead anchor configuration preferably reduces the opportunities for such lead damage.

Securing the lead in place should be simple, to reduce surgical time, and evident, to limit chances for error. The lead anchor is preferably slidable along the lead so it may be positioned appropriately for different implant locations and for a variety of patient body types. Multiple lead anchors per lead cable may be useful in some situations.

The lead anchor is preferably compact and light-weight, and constructed of biocompatible materials. Once properly secured, the connection between the anchor and lead cable should be strong enough to resist pulling and any other forces that could unintentionally disconnect the lead cable from the surrounding tissue.

There exists a need in the art for a compact, easy to operate, fast, and reliable way to secure a tube or cable, such as a lead cable, to surrounding tissue that limits the likelihood of damage to the tube or cable.

BRIEF SUMMARY OF THE INVENTION

The present invention addresses the above and other needs by providing an anchor for securing lead cables, i.e., leads or lead extensions, or other cables or tubular members within a body. The device of the present invention preferably applies to a lead with electrodes at one end of the lead. The other end of the lead is typically detachably connected to a lead extension. Alternatively, the invention applies to the lead extension that is typically detachably connected to the lead at one end and to a medical device at the other end. Furthermore, the invention may apply to any conduit, cable, tube, or other elongated, cylindrical member that is to be secured in a body.

The lead anchor of the present invention preferably comprises two coaxially arranged sleeves and a coaxial spring. The sleeves preferably include suture holes that allow the anchor to be secured to the surrounding tissue. A channel is preferably provided in each sleeve, allowing the spring to be secured at one end to one sleeve and at the other end to the second sleeve. The sleeves also include a locking mechanism that holds the sleeves in at least one, but preferably in two or more positions relative to each other. The locking mechanism preferably comprises a protrusion on and/or in one sleeve that fits into one of two or more recesses on and/or in the other sleeve. As the sleeves are rotated in relation to each other, the protrusion settles into one or the other of these recesses.

As one sleeve is rotated in relation to the other, the spring is also twisted, which causes the inner diameter of the spring to increase or decrease. The locking mechanism thus holds the spring in one of a variety of positions with one of a variety of inner diameters. For instance, by rotating one sleeve until the protrusion fits into one of the recesses, the spring is held in a position that releases the lead cable. Rotating the sleeve in the other direction causes the inner diameter of the spring to decrease, which in turn causes the spring to grip the lead cable. The sleeves may be locked into this position with the protrusion settled into a different recess. Once locked in this position, the lead anchor may be secured to the surrounding tissue.

Thus, the present invention allows easy locking and unlocking of the anchor onto the lead cable without a need for sutures. Anther advantage, inter alia, of the lead anchor of the present invention is its simple design, and its small size. The lead anchor may be activated with fingers or with tools. Improved control and load distribution result from some embodiments of the invention. The simple and sure mechanism of the present invention thus results in reduced surgical time and possible error, while ensuring a secure hold between the anchor and lead cable, and to the surrounding tissue.

BRIEF DESCRIPTION OF THE DRAWINGS

The above and other aspects, features, and advantages of the present invention will be more apparent from the following more particular description thereof, presented in conjunction with the following drawings wherein.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1A:
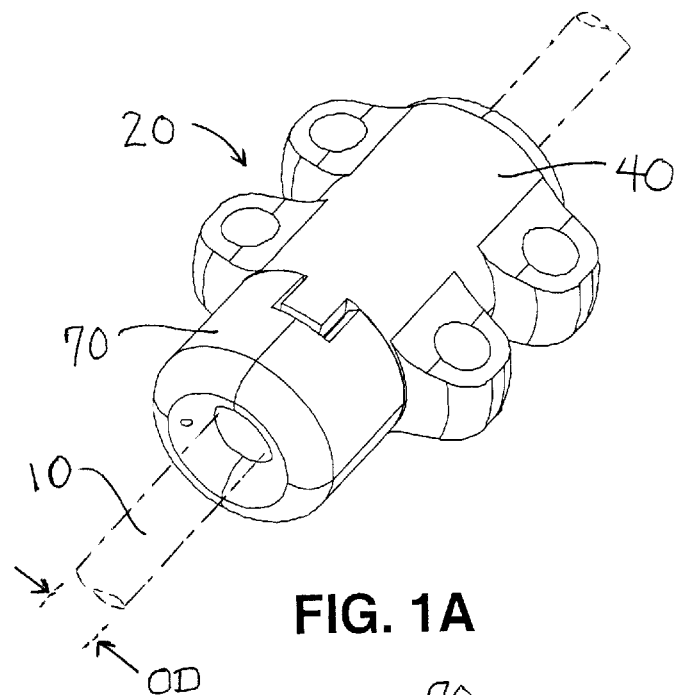
FIG. 1A is a trimetric view of a lead anchor of an embodiment of the present invention and a lead cable of the type that may be used with the present invention.

For illustration purposes, the following description of the present invention is shown in conjunction with an implantable lead cable 10 (i.e., lead, lead extension, or lead system), shown, e.g., in FIG. 1A. It is to be understood, however, that the invention could also be used to secure a drug-delivery tube, or other elongated cylindrical member, that has the same general form as the lead cable 10. An implantable lead typically connects electrode arrays or other devices at and/or along the distal end of the lead to a detachably connected lead extension at the proximal end of the lead. The other end of the lead extension is typically removably connected to a medical device. An illustration of such a connection is found in U.S. Provisional Patent Application Serial No. 60/145,829, filed Jul. 27, 1999, which application is incorporated herein by reference. Lead cable 10 preferably has a circular outer diameter OD of about 1.35 mm (0.053 inch), although those of skill in the art will see that the lead anchor of the present invention may be modified to work with lead cables or tubes having diameters that are either smaller or larger than this.

A lead typically comprises lead wires within a lead cable, with electrode array(s) or other device(s) at and/or along its distal end. At the proximal end of the lead is a lead connector (not shown), which is typically removably connected to a lead extension or medical device. The lead extension, when used, is typically removably connected to the medical device. The lead connector may also be removably connected directly to the medical device to form the electromechanical connection between the components inside the device and lead wires within the lead. At the distal end (not shown) of the lead, or along the length of the lead, there will typically be an array of electrodes, or other components (e.g., one or more sensors) to which the components within the medical device are electrically connected. It is the function of lead cable(s) 10 to connect the distal electrodes/sensor(s) to the assembly housed within the device, thereby allowing the device to perform its intended function (e.g., neuro-stimulation, sensing, monitoring, or the like). An exemplary neuro-stimulator systems is shown, e.g., in previously-referenced U.S. Provisional Patent Application Serial No. 60/145,829, filed Jul. 27, 1999.

Figure 1B:
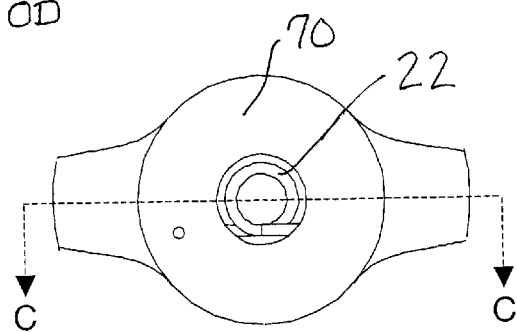
FIG. 1B is an end view of the lead anchor of FIG. 1A.
Figure 1C:
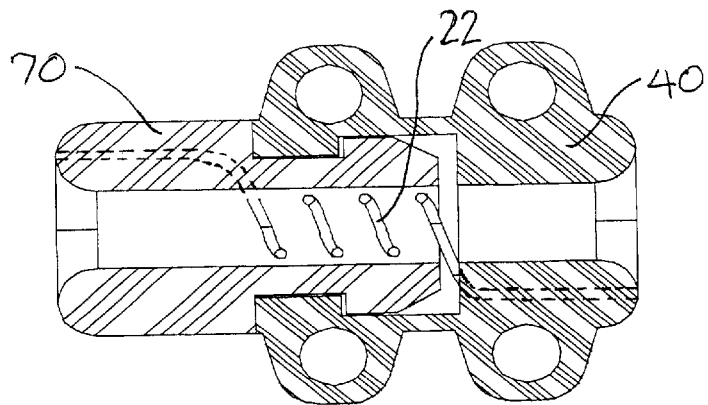
FIG. 1C is a section view of the lead anchor of FIG. 1B, taken along section plane C—C of FIG. 1B.

A preferred lead anchor 20 of the present invention is shown in FIG. 1A, surrounding a portion of lead cable or tube 10. Lead anchor 20 preferably comprises two sleeves, for instance, outer sleeve 40 and inner sleeve 70. As can be seen in FIGS. 1B and 1C, a portion of inner sleeve 70 preferably fits within outer sleeve 40, as will be described in more detail presently.

Also shown in FIGS. 1B and 1C is a spring 22 located within lead anchor 20. Spring 22 is preferably secured at one end to outer sleeve 40 and at the other end to inner sleeve 70. The inner diameter of spring 22 (in a relaxed state) is preferably slightly smaller than the outer diameter of lead cable 10. For instance, for a lead cable with a 1.35 mm (0.053 inch) outer diameter OD, the inner diameter ID of spring 22 (FIG. 4D) is preferably within the range of 1.09 mm (0.043 inch) to 1.19 mm (0.047 inch), and more preferably about 1.14 mm (0.045 inch). However, as mentioned above, the inner diameter of spring 22 may be larger or smaller to accommodate different sized lead cables or tubes.

Outer sleeve 40 is shown in more detail in FIGS. 2A through 2E. Outer sleeve 40 is preferably configured to allow suture material to be secured to the lead anchor, so that the anchor may then be secured to surrounding tissue. In this preferred embodiment, four tabs 42 extend radially from the sides of the outer sleeve's main body, and are arranged in pairs that are preferably but not necessarily directly opposite each other. Suture holes 44 extend through the tabs, to allow suture(s) to be passed through the suture holes in the tabs and secured to the tissue. Alternatively, both outer sleeve 40 and inner sleeve 70 may be configured with tabs or the equivalent to allow securing with suture material. Furthermore, a variety of configurations other than tabs with holes are possible (and will be evident to those of skill in the art), such as hooks, slots, indentations, or other surface features or textures.

A protrusion 48 is preferably located at the end of outer sleeve 40 that faces inner sleeve 70. As described below, this protrusion is associated with one or more recesses in inner sleeve 70 that preferably allow lead anchor 20 to be locked into a fixed position or released into a free position. Additional protrusions 48 may be used, if desired.

Outer sleeve 40 is preferably made of a molded, soft polyurethane, such as Tecothane® polyether-based thermoplastic polyurethane (available from Thermedics Inc., Woburn, Mass.), and most preferably 85A Tecothane® material, which results in protrusion 48 being flexible and resilient, may be used instead or in addition. As will become apparent, this is a desirable property for protrusion 48. Other materials, such as epoxy or silicone, may be used, as will be recognized by those of skill in the art. In addition, sleeves 40 and 70 may be made of multiple materials.

Figure 2A:
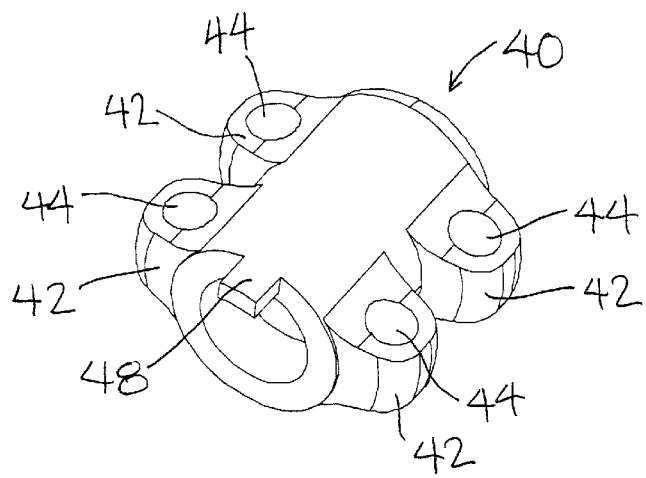
FIG. 2A is a trimetric view of a first sleeve of the lead anchor of FIG. 1A.
Figure 2B:
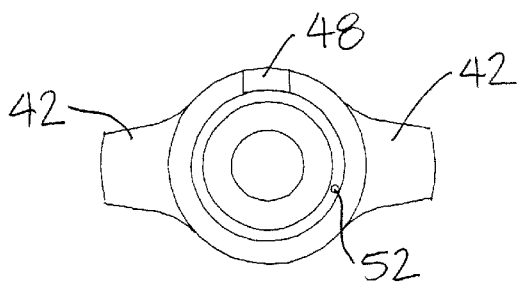
FIG. 2B is an end view of one end of the sleeve of FIG. 2A.
Figure 2C:
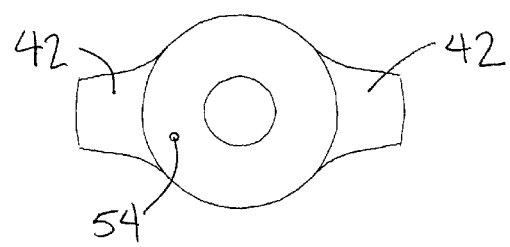
FIG. 2C is an end view of the other end of the sleeve of FIG. 2A.
Figure 2D:
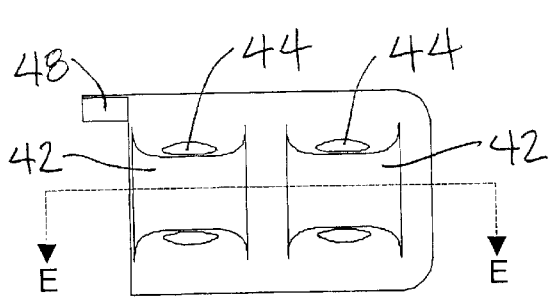
FIG. 2D is a side view of the sleeve of FIG. 2A.
Figure 2E:
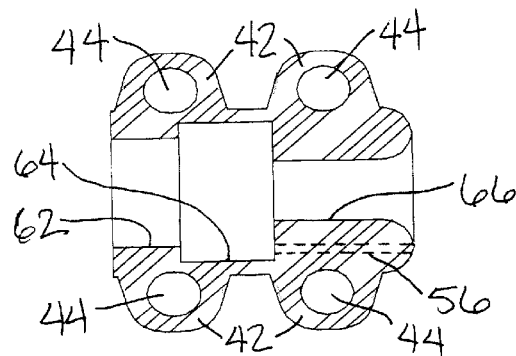
FIG. 2E is a section view of the sleeve of FIG. 2D, taken along section plane E—E of FIG. 2D.

FIGS. 2B and 2C show outer sleeve spring holes 52 and 54, respectively. Spring hole 52 allows insertion of one end of spring 22. If any of the spring wire protrudes from spring hole 54, it is preferably cut flush with the end of outer sleeve 40. Alternatively, spring 22 may be made with short enough ends that spring hole 54 is not necessary. As indicated in FIG. 2E, an outer sleeve spring channel 56 extends through outer sleeve 40 between spring holes 52 and 54. Once the lead anchor is assembled, the wire extending from one end of spring 22 will be held in channel 56.

As can best be seen in FIGS. 1C and 2E, the inner diameter of outer sleeve 40 varies. From the side closest to inner sleeve 70, outer sleeve 40 has two different inner diameters 62 and 64 matching the outer diameters of two sections of inner sleeve 70 that fit into outer sleeve 40. The inner diameter 66 of the portion of outer sleeve 40 that is farthest from inner sleeve 70 is preferably slightly larger than the outer diameter of the lead cable to be anchored.

Inner sleeve 70 is shown in FIGS. 3A through 3F. Inner sleeve 70 may be configured with suture holes or the like. However, in the preferred embodiment depicted in FIGS. 1A through 3F, the suture holes are positioned on outer sleeve 40. As mentioned earlier, a variety of lead anchor configurations will allow securing with suture material.

Figure 3A:
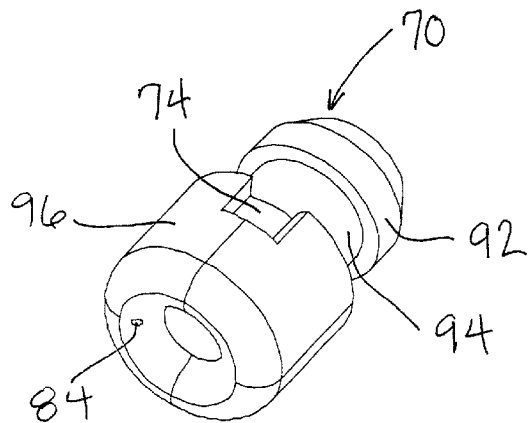
FIG. 3A is a trimetric view of a second sleeve of the lead anchor of FIG. 1A.
Figure 3B:
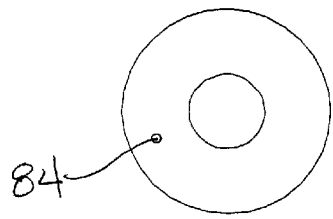
FIG. 3B is an end view of one end of the sleeve of FIG. 3A.
Figure 3C:
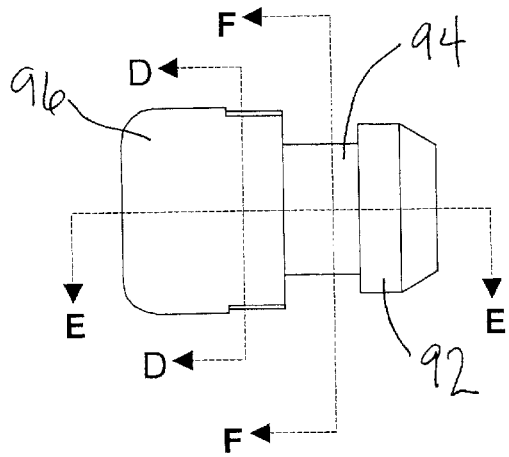
FIG. 3C is a side view of the sleeve of FIG. 3A.
Figure 3D:
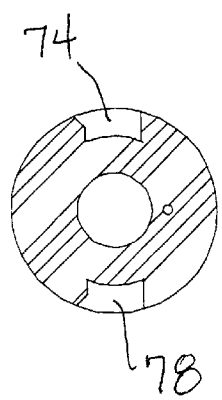
FIG. 3D is a section view of the sleeve of FIG. 3C, taken along section plane D—D of FIG. 3C.

Recess 74 and recess 78 are best seen in FIGS. 3A and 3D. As mentioned earlier, protrusion 48 on outer sleeve 40 preferably fits into a recess, which preferably locks lead anchor 20 into a fixed position or releases the anchor, allowing it to slide axially on the lead cable. This will be described in more detail presently. Inner sleeve 70 is preferably, but not necessarily, made of the same material(s) as outer sleeve (i.e. preferably a molded, soft polyurethane, such as Tecothane® material). In one alternative, inner sleeve 70 is made of a harder material, such as epoxy.

Figure 3E:
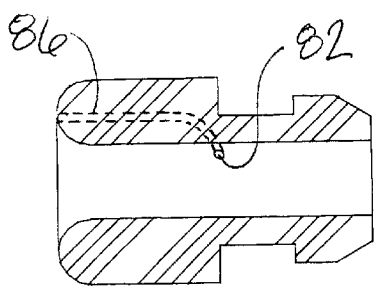
FIG. 3E is a section view of the sleeve of FIG. 3C, taken along section plane E—E of FIG. 3C.
Figure 3F:
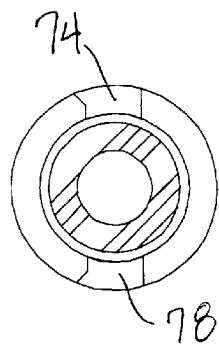
FIG. 3F is a section view of the sleeve of FIG. 3C, taken along section plane F—F of FIG. 3C.

FIGS. 3E and 3B show inner sleeve spring holes 82 and 84, respectively. Spring hole 82 allows insertion of one end of spring 22. If any of the spring wire protrudes from spring hole 84, is preferably cut flush with the end of inner sleeve 70. Alternatively, spring 22 may be made with short enough ends that spring hole 84 is not necessary. As indicated in FIG. 3E, an inner sleeve spring channel 86 extends through inner sleeve 70 between spring holes 82 and 84. Once the lead anchor is assembled, the wire extending from one end of spring 22 will be held in channel 86.

As can best be seen in FIGS. 1C and 3A, the outer diameter of inner sleeve 70 varies. The side of inner sleeve 70 closest to outer sleeve 40 preferably has a plug-type configuration. Plug section 92 closest to outer sleeve 40 preferably increases in diameter until the portion of section 92 away from outer sleeve 40 is slightly less than the inner diameter 64 of outer sleeve 40. Section 94 of inner sleeve 70 is preferably slightly smaller than the inner diameter 62 of outer sleeve 40. The outer diameter of section 96 of inner sleeve 70 is preferably similar to the diameter of the body of the outer sleeve 40. The inner diameter of inner sleeve 70 is preferably slightly larger than the outer diameter of the lead cable to be anchored.

Figure 4A:
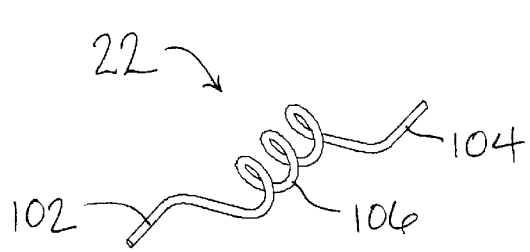
FIG. 4A is a trimetric view of a spring for use with a lead anchor of the invention.
Figure 4B:
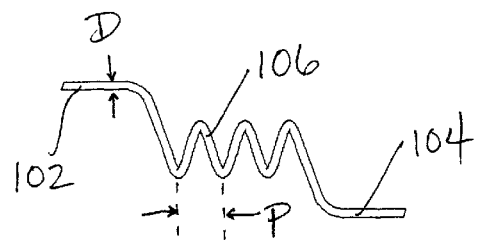
FIG. 4B is a top view of the spring of FIG. 4A.
Figure 4C:
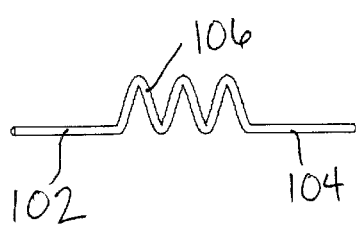
FIG. 4C is a side view of the spring of FIG. 4A.
Figure 4D:
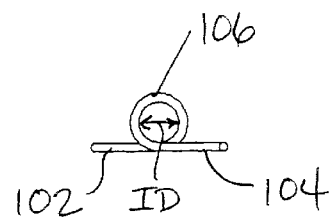
FIG. 4D is an end view of the spring of FIG. 4A.
Figure 4E:
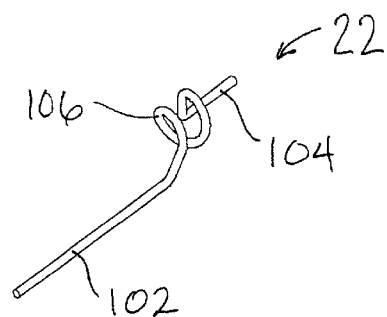
FIG. 4E is a trimetric view of an alternate spring for use with a lead anchor of the invention.

Preferred embodiments of spring 22 are shown in FIGS. 4A through 4E. Spring 22 is preferably but not necessarily made of round wire, and preferably has sections 102 and 104 that extend from either end of a wound section 106. As best seen in FIGS. 4A and 4E, wound section 106 may include any number of coils, such as three (FIG. 4A), or two (FIG. 4E). Sections 102 and 104 are preferably straight, may be the same or different lengths, are preferably parallel to the axis of spring 22, and are preferably offset from one another. Alternatively, there may be bend(s), loop(s), or similar feature(s) along or at the ends of one or both sections 102 and 104. For instance, a loop may either extend about the axis or along the axis of the anchor. Such features may advantageously improve the ability of the lead anchor to resist linear and rotational forces, disassembly, or other distortion or failure. Such features on sections 102 or 104 may extend beyond one or both ends of the assembled lead anchor, or may be fixed inside the inner and outer sleeves. Alterations to holes 52, 54, 82 and 84, channels 56 and 86, and also possibly fabrication and/or assembly of the lead anchor may be necessary with these alternative spring configurations. In addition, in some alternatives, the sleeves may abut each other rather than having one sleeve fit inside the other sleeve.

Spring 22 is preferably a helical spring, and more preferably is a torsion spring. Other types of springs (e.g., compression, extension, etc.) may alternatively be used to achieve the result described presently. As mentioned above, sections 102 and 104 preferably extend parallel to the axis of the spring, whereas the ends of typical torsion springs generally extend radially (or near so) from the axis of the spring. In addition, spring 22 preferably has space between coils (FIG. 1C, 4A–4C, 4E), whereas torsion springs typically are wound with no space between coils of the spring (i.e., they are close wound). In a preferred embodiment, the pitch P of wound section 106 is between 0.76 mm (0.03 inch) and 1.27 mm (0.05 inch), and more preferably about 1 mm (0.039 inch). However, more typical torsion spring configurations could also be used with the present invention, as could a variety of other spring designs.

The material properties, cross-sectional geometry, and other dimensions of the spring wire are such that the spring is strong enough to endure assembly, handling, and use, while being as unobtrusive as possible. Thus, spring 22 is preferably made of a biocompatible material, more preferably of a durable medical grade metal, and most preferably MP35N wire or 316 stainless steel wire. The wire diameter D is preferably between 0.18 mm (0.007 inch) and 0.381 mm (0.015 inch), and more preferably about 0.25 mm (0.01 inch). To impart to the spring characteristics necessary for use as described below, the spring is preferably wound and spring-tempered via standard means known to those of ordinary skill in the art. The result is preferably a spring with an inner diameter that is slightly smaller than the outer diameter of the lead cable, as described earlier. Advantageously, the size of the inner diameter of the spring results in different amounts of tension which may be useful in various situations.

Spring 22 preferably grips the lead cable when lead anchor 20 is set in a certain locked position. In operation, outer sleeve 40 is rotated about its axis relative to inner sleeve 70 (e.g. clockwise). Alternatively, inner sleeve 70 may be rotated relative to outer sleeve 40, or both sleeves may be rotated at the same time. Relative rotation in one direction (e.g. clockwise) preferably causes protrusion 48 to settle into recess 74, while rotation in the other direction (e.g. counter-clockwise) preferably causes protrusion 48 to settle into recess 78. Protrusion 48 (and possibly all or some of outer sleeve 40) is thus preferably made of a flexible material, so protrusion 48 can ride along the outer diameter of section 96 of inner sleeve 70 until it reaches a recess.

A variety of locking schemes are possible, as will be apparent to one of skill in the art. For instance, a pin and receptacle mechanism may be used, or a slot and detent system, or raised features that fit into indentations. A gear type mechanism may allow a variety of settings for various sized lead cables and/or a variety of tension settings. In addition, the locking mechanism of the previously described preferred embodiment may include additional protrusions and/or additional recesses, which may increase the strength of the mechanism or may increase the positions at which the spring may be set. Alternatively, the anchor may have only one recess, it is not necessary to hold the spring when it is in a relaxed state. In a preferred case where the spring is relaxed when it is gripping the lead cable, a recess for holding the spring while sliding the anchor on the lead cable would still be desired. However, if the anchor was able to move on the lead cable when the spring was in a relaxed state, a recess would be desired for holding the spring while it is gripping the lead cable. These and other alternatives may be used with the lead anchor of the present invention without departing from the spirit of the invention.

Figure 5A:
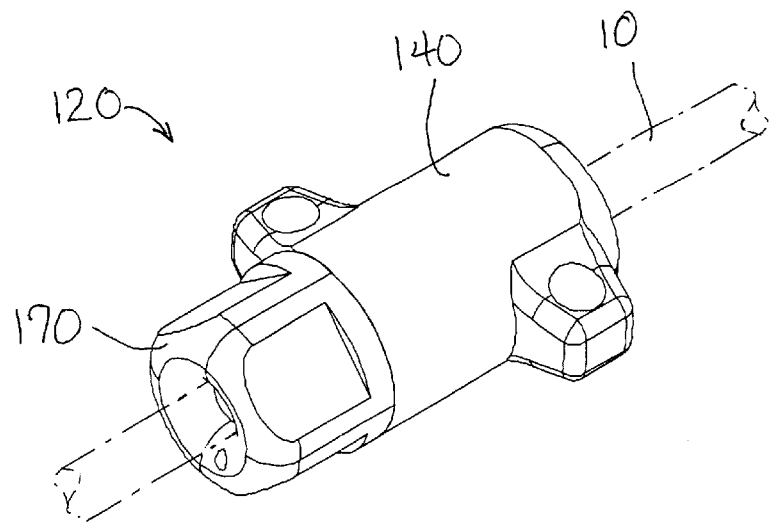
FIG. 5A is a trimetric view of a lead anchor of another embodiment of the present invention and a lead cable of the type that may be used with the present invention.
Figure 5B:
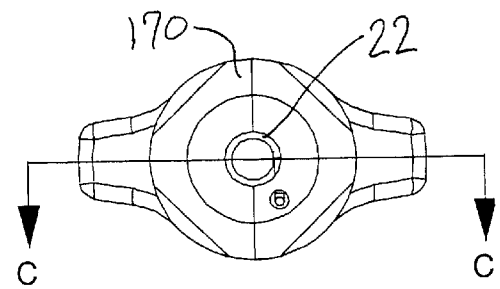
FIG. 5B is an end view of the lead anchor of FIG. 5A.
Figure 5C:
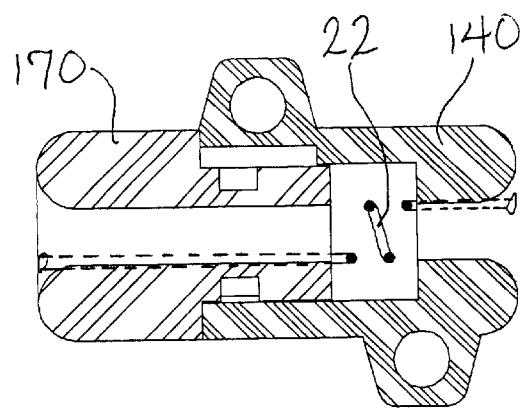
FIG. 5C is a section view of the lead anchor of FIG. 5B, taken along section plane C—C of FIG. 5B.

For example, an additional preferred lead anchor 120 of the present invention is shown in FIG. 5A. As with lead anchor 20, lead anchor 120 preferably comprises two sleeves, for instance, outer sleeve 140 and inner sleeve 170. As can be seen in FIGS. 5B and 5C, a portion of inner sleeve 170 preferably fits within outer sleeve 140, as will be described in more detail presently.

Also shown in FIGS. 5B and 5C is a spring 22 located within lead anchor 120. Spring 22 is preferably secured at one end to outer sleeve 140 and at the other end to inner sleeve 170. Once again, the inner diameter of spring 22 (in a relaxed state) is preferably slightly smaller than the outer diameter of lead cable 10, and may be changed to accommodate different sized lead cables or tubes.

Figure 6A:
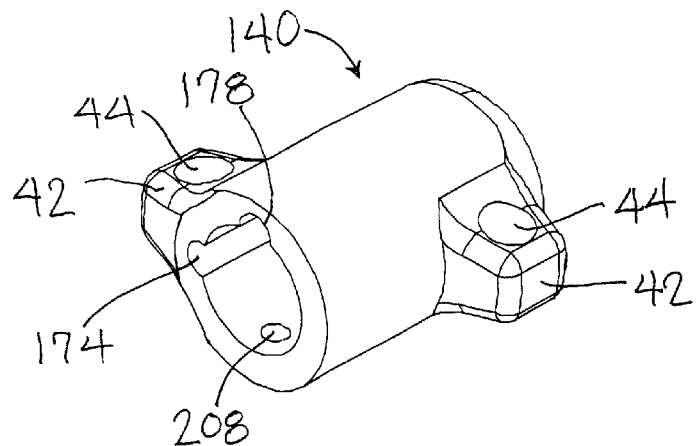
FIG. 6A is a trimetric view of a first sleeve of the lead anchor of FIG. 5A.
Figure 6B:
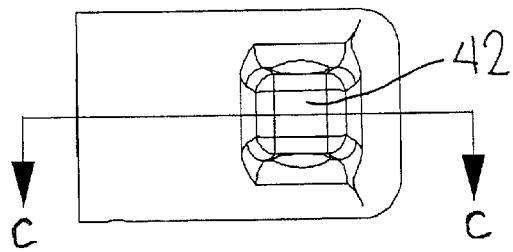
FIG. 6B is a side view of the sleeve of FIG. 6A.
Figure 6C:
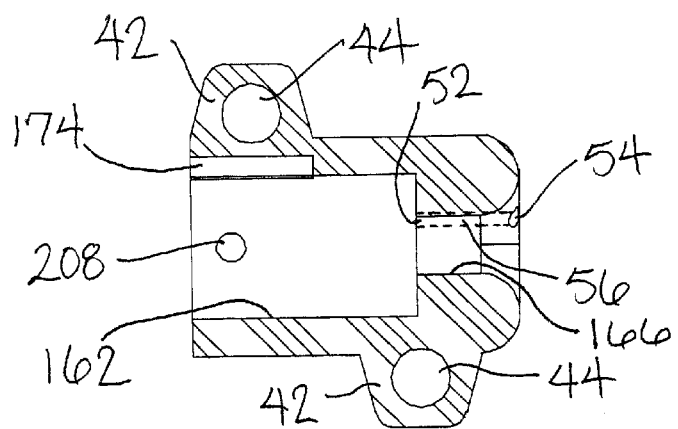
FIG. 6C is a section view of the sleeve of FIG. 6B, taken along section plane C—C of FIG. 6B.

Outer sleeve 140 is shown in more detail in FIGS. 6A through 6C. In this preferred embodiment, two tabs 42 extend radially from the sides of the outer sleeve's main body, and are arranged so that they are preferably but not necessarily offset from each other. Suture holes 44 extend through the tabs, to allow suture(s) to be passed through the suture holes in the tabs and secured to the tissue. In one alternative, both outer sleeve 140 and inner sleeve 170 may be configured with tabs or the equivalent to allow securing with suture material.

Figure 7A:
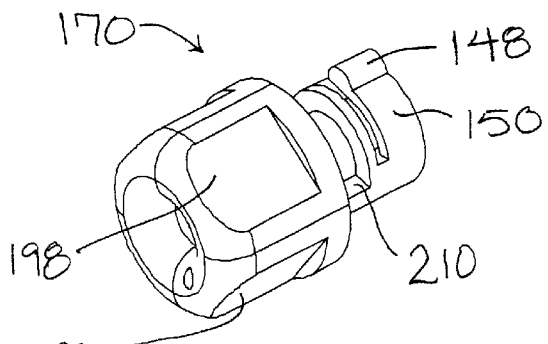
FIG. 7A is a trimetric view of a second sleeve of the lead anchor of FIG. 5A.
Figure 7B:
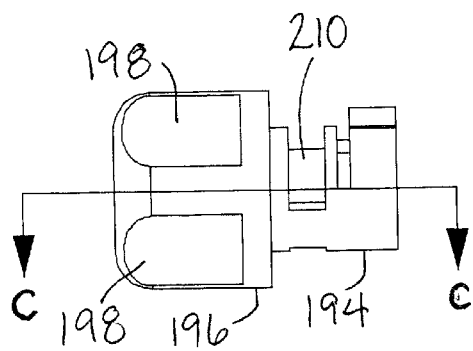
FIG. 7B is a side view of the sleeve of FIG. 7A.
Figure 7C:
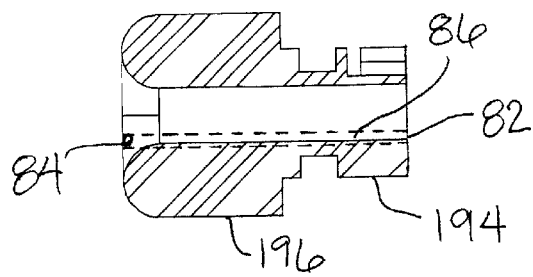
FIG. 7C is a section view of the sleeve of FIG. 7B, taken along section plane C—C of FIG. 7B.

Inner sleeve 170 is shown in FIGS. 7A through 7C. A protrusion 148 is preferably located at the end of a cantilevered section 150 of inner sleeve 170 that faces outer sleeve 140. As described below, protrusion 148 is associated with one or more recesses in outer sleeve 140 that preferably allow lead anchor 120 to be locked into a fixed position or released into a free position. Additional protrusions 148 may be used, if desired.

Outer sleeve 140 and inner sleeve 170 are preferably made from a high purity (e.g., medical grade) epoxy casting system, such as Hysol® resin EE0079 and hardener HD0070 (as manufactured by Dexter Corporation of Windsor Locks, Conn. and available from Dexter Electronics Material Division of Olean, N.Y.), which results in protrusion 148 being relatively hard. Other materials, such as a silicone or a soft polyurethane, such as Tecothane® polyether-based thermoplastic polyurethane, may be used, as will be recognized by those of skill in the art. In addition, sleeves 140 and 170 may be made of multiple materials.

As with anchor 20, the end sections 102 and 104 of spring 22 are similarly positioned in channels in the inner and outer sleeves of anchor 120. FIGS. 5C and 6C best show outer sleeve 140 spring holes 52 and 54, with outer sleeve spring channel 56 extending through outer sleeve 140 between spring holes 52 and 54. FIGS. 5C and 7C best show inner sleeve 170 spring holes 82 and 84, with inner sleeve spring channel 86 extending through inner sleeve 170 between spring holes 82 and 84.

As can best be seen in FIGS. 5C and 6C, the inner diameter of outer sleeve 140 varies. On the side closest to inner sleeve 170, outer sleeve 140 has an inner diameter 162 coordinated with an outer diameter 194 of inner sleeve 170 (FG. 7C) that fits into outer sleeve 140. The inner diameter 166 of the portion of outer sleeve 140 that is farthest from inner sleeve 170 is preferably slightly larger than the outer diameter of the lead cable to be anchored.

As can best be seen in FIGS. 5C, 7B, and 7C, the outer diameter of inner sleeve 170 varies. Section 194 of inner sleeve 170 preferably has an outer diameter that is slightly smaller than inner diameter 162 of outer sleeve 140. The outer diameter of section 196 of inner sleeve 170 is preferably similar to the outer diameter of the body of outer sleeve 140. In addition, section 196 of inner sleeve 170 preferably includes flat portions 198 (FIGS. 7A and 7B), which are provided to improve gripping inner-sleeve 170 with fingers, or with a tool. The inner diameter of inner sleeve 170 is preferably slightly larger than the outer diameter of the lead cable to be anchored.

Recess 174 and recess 178 are best seen in FIGS. 6A and 6C. As mentioned earlier, protrusion 148 on inner sleeve 170 preferably fits into a recess, which preferably locks lead anchor 120 into a fixed position or releases the anchor, allowing it to slide axially on the lead cable.

Spring 22 preferably grips the lead cable when lead anchor 120 is set in a certain locked position. In operation, outer sleeve 140 is rotated about its axis relative to inner sleeve 170 (e.g. clockwise). Alternatively, inner sleeve 170 may be rotated relative to outer sleeve 140, or both sleeves may be rotated at the same time. Relative rotation in one direction (e.g. clockwise) preferably causes protrusion 148 to settle into recess 174, while rotation in the other direction (e.g. counter-clockwise) preferably causes protrusion 148 to settle into recess 178. Protrusion 148 is thus preferably positioned at the end of a cantilevered section 150, which can therefore flex while protrusion 148 rides along the inner diameter of section 162 of outer sleeve 140 until it reaches a recess.

Figure 8:
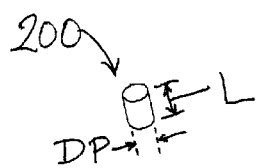
FIG. 8 is a trimetric view of a pin of the lead anchor of FIG. 5A.

A pin 200, as shown in FIG. 8, is preferably provided to help secure or fasten the sleeves together. Pin 200 diameter DP is preferably between 0.635 mm (0.025 inch) and 0.900 mm (0.035 inch), and more preferably about 0.760 mm (0.030 inch). Pin 200 length L is preferably between 0.900 mm (0.035 inch) and 1.145 mm (0.045 inch), and more preferably about 1.015 mm (0.040 inch). Pin 200 is preferably made of a medical grade metal, such as 316 stainless steel.

In a preferred configuration, a hole 208 (FIGS. 6A and 6C) is provided in outer sleeve 140 and a slot 210 (FIGS. 7A and 7B) is provided in inner sleeve 170, for use with pin 200. Once portion 194 of inner sleeve 170 is inserted into portion 162 of outer sleeve 140, pin 200 is inserted into hole 208. Pin 200 is preferably held in hole 208 via an interference fit, however other options are possible, such as alternative or additional use of adhesive. Pin 200 is inserted into hole 208 until the proximal end of the pin is flush with the outer surface of outer sleeve 140. As a result, the distal end of pin 200, once inserted, extends into slot 210 of inner sleeve 170. As the sleeves are rotated in relation to one another, the pin travels along slot 210 and prevents the sleeves from moving apart. Other comparable fastening configurations are possible, such as having features on both sleeves that allow them to snap together.

In the above preferred embodiments, when the sleeves are rotated relative to one another to cause locking of the anchor in one position, spring 22 is twisted so that the inner diameter of the spring is decreased. The decreased inner diameter of the spring in this position is slightly smaller than the outer diameter of the lead cable, thus the coils of the spring grip the lead cable. Preferably but not necessarily, the spring is in a relaxed state when the lead anchor is in this locked position. Given that the spring is relaxed when it grips the lead cable (or similar), it is not necessary to provide a locking mechanism in this position, but it is presently considered preferable. When the sleeves are rotated relative to one another to cause releasing of the anchor from the lead cable, spring 22 is twisted so that the inner diameter of the spring is increased. The increased inner diameter of the spring in this position is slightly greater than the outer diameter of the lead cable, thus the anchor is allowed to slide axially on the lead cable. Thus, relative rotation of the sleeves twists the ends of the spring, which in turn varies the inner diameter of the spring so that it either grips or releases the lead cable. As such, any type or combination of springs that can be used in this way is suitable.

As mentioned above, each sleeve is preferably molded, although other processes, such as casting, may be used. Channels 56 and 86 are preferably formed during the molding process, as are any grooves for guiding the spring into place or any other features desired in the sleeves. Alternatively, any holes, channels, grooves, etc. may be formed (e.g. drilled) after molding of the sleeves. In one alternative, the spring is assembled into the anchor by sliding sections 102 and 104 into channels 56 and 86. Thus, spring sections 102 and 104 and channels 56 and 86 are preferably straight. If spring sections 102 and 104 (and also preferably channels 56 and 86) have bends in them, the sleeve material may still allow sections 102 and 104 to be slid into place in channels 56 and 86. In another alternative, holes such as holes 52, 54, 82 and 84, and channels such as channels 56 and 86 are preferably not provided, and spring sections 102 and 104 are instead forced through the material of the sleeves. In the case of relatively soft Tecothane® material, for example, this is one of the preferred techniques.

Alternatively, the sleeves (or at least one sleeve) may be molded in place over spring section(s) 102 and 104. In yet another alternative, a portion of one or both sleeves may be molded, then the spring may be put in place, and an over-mold may further secure the end(s) of the spring within the sleeve(s). The process of over-molding is known to those of skill in the art. This process may advantageously be combined with a spring having a bend or bends, loops, or other feature at one or both ends.

An advantage, inter alia, of the lead anchor of the present invention is its simplicity of both design and use, and its associated small size. The lead anchor may be activated with the fingers or with tools. While sutures are often required to hold a lead anchor onto a lead cable, the present invention allows easy locking of the anchor onto the lead cable without a need for sutures. In some embodiments, the present invention also offers better control and better load distribution than previous methods and mechanisms. The simple and sure mechanism of the present invention thus results in reduced surgical time and possible error, while ensuring a secure hold between the anchor and lead cable, and to the surrounding tissue.

Thus, the invention provides a simple, yet reliable and easy-to-use approach for securing an implantable lead cable or similar structure, e.g. a tube, within a body. The lead anchor of the present invention also provides a secure and evident connection to the lead cable without necessary use of a tool(s), thus reducing surgery time, risk of infection, and likelihood of error. With the anchor in place, the lead cable advantageously resists flexing and other forces, yet the anchor is compact and light-weight.

In yet another embodiment, the present invention may be used to secure a tube or any other implantable elongated cylindrical member with a shape similar to lead 10. Therefore, reference number 10 in FIG. 1A may depict a tube, cord, conduit, duct, wire, cable, fiber optics or other implantable item, rather than a lead. For instance, a tube may be used to deliver a medication from an implanted or an external device to a specific location in the body.

While the invention herein disclosed has been described by means of specific embodiments and applications thereof, numerous modifications and variations could be made thereto by those skilled in the art without departing from the scope of the invention set forth in the claims. For example, other lead anchor shapes, sizes, and configurations will be apparent to those of skill in the art, such as an anchor lacking the advantages of suture holes. Likewise, the sleeves of the anchor may have indentations rather than holes for sutures. Additional alternatives will be apparent to those skilled in the art, from reading the specification and reviewing the drawings herein, without deviating from the spirit of the instant invention.

What is claimed is:

1. An implantable lead system comprising:
   at least one lead cable; and
   at least one lead anchor slidable along at least a portion of the lead cable;
   wherein the at least one lead anchor comprises:
   a first sleeve;
   a second sleeve;
   a spring secured at one end to the first sleeve and at the other end to the second sleeve; and
   a locking mechanism to hold the first sleeve and the second sleeve in at least one locked position;
   wherein rotation of the first sleeve relative to the second sleeve causes an inner diameter of the spring to change;
   wherein the rotation activates the locking mechanism; and
   wherein the spring is configured so the inner diameter of the spring can grip the lead cable.

2. The lead system of claim 1 further configured so that the spring in a relaxed state has an inner diameter slightly smaller than the outer diameter of the lead cable.

3. The lead system of claim 1 further configured so that the rotation in one direction causes the inner diameter of the spring to increase, wherein the spring releases the lead cable.

4. The lead system of claim 1 wherein an edge of the first sleeve abuts an edge of the second sleeve prior to the rotation and also subsequent to the rotation.

5. The lead system of claim 1 wherein at least a portion of the first sleeve is fitted over at least a portion of the second sleeve.

6. The lead system of claim 1 further comprising at least one suture hole for suturing the lead anchor within a body.

7. The lead system of claim 1 wherein the spring is a helical spring.

8. The lead system of claim 7 wherein the helical spring is a torsional spring.

9. The lead system of claim 7 wherein the spring has straight offset ends.

10. The lead system of claim 1 wherein the first sleeve defines a slot and wherein the second sleeve defines a hole and further comprising a pin insertable in the hole such that the pin travels in the slot during rotation of the first sleeve relative to the second sleeve.

11. An implantable lead system comprising:
   at least one lead cable; and
   at least one lead anchor slidable along at least a portion of the lead cable;
   wherein the at least one lead anchor comprises:
      a first sleeve;
      a second sleeve;
      a spring secured at one end to the first sleeve and at the other end to the second sleeve; and
      a locking mechanism to hold the first sleeve and the second sleeve in at least one locked position;
   wherein rotation of the first sleeve relative to the second sleeve causes an inner diameter of the spring to change;
   wherein the rotation activates the locking mechanism; and
   wherein the locking mechanism defines at least one protrusion on the first sleeve and at least one recess on the second sleeve, wherein the rotation of the first sleeve relative to the second sleeve causes the at least one protrusion to settle into the at least one recess.

12. The lead system of claim 11 wherein the spring is configured so the inner diameter of the spring can grip the lead cable.

13. An implantable lead system comprising:
   at least one lead cable; and
   at least one lead anchor slidable along at least a portion of the lead cable;
   wherein the at least one lead anchor comprises:
      a first sleeve;
      a second sleeve;
      a spring secured at one end to the first sleeve and at the other end to the second sleeve; and
      a locking mechanism to hold the first sleeve and the second sleeve in at least one locked position;
   wherein rotation of the first sleeve relative to the second sleeve causes an inner diameter of the spring to change;
   wherein the rotation activates the locking mechanism; and
   wherein the locking mechanism comprises more than one locked position.

14. An anchor for anchoring an implantable elongated cylindrical member within a body, the anchor comprising:
   a first sleeve;
   a second sleeve;
   a spring secured at one end to the first sleeve and at the other end to the second sleeve, the spring in a relaxed state having a inner diameter slightly smaller than the outer diameter of the cylindrical member; and
   a locking mechanism to hold the first sleeve and the second sleeve in at least one locked position;
   wherein rotation of the first sleeve relative to the second sleeve causes the inner diameter of the spring to increase, the spring thereby releasing the cylindrical member; and
   wherein the rotation activates the locking mechanism, thereby locking the first sleeve and second sleeve in position while the anchor is free to move along the cylindrical member.

15. The anchor of claim 14 further comprising at least one suture hole for suturing the anchor within a body.

16. The anchor of claim 14 wherein the locking mechanism defines at least one protrusion on the first sleeve and at least one recess on the second sleeve, wherein the rotation of the first sleeve relative to the second sleeve causes the at least one protrusion to settle into the at least one recess.

17. The anchor of claim 14 wherein the first sleeve defines a slot and wherein the second sleeve defines a hole and further comprising a pin insertable in the hole such that the pin travels in the slot during rotation of the first sleeve relative to the second sleeve.

18. The anchor of claim 14 wherein the cylindrical member is at least one of a tube, cord, conduit, duct, wire, cable, lead, fiber optic or fiber optic assembly.

19. The anchor of claim 14 wherein the spring is a helical spring.

20. The anchor of claim 19 wherein the helical spring is a torsional spring.

21. A method of forming an anchor for an implantable elongated cylindrical member, comprising:
   forming a first sleeve coaxial with and slidable along the cylindrical member;
   forming a second sleeve coaxial with and slidable along the cylindrical member;
   securing one end of a spring to the first sleeve and securing the other end of the spring to the second sleeve; and
   providing a locking mechanism to hold the first sleeve and the second sleeve in at least one locked position;
   wherein rotating the first sleeve relative to the second sleeve causes an inner diameter of the spring to change;
   wherein the rotating causes activation of the locking mechanism; and
   wherein the spring is configured so the inner diameter of the spring can grip the cylindrical member.

22. The method of claim 21 wherein the spring in a relaxed state has an inner diameter slightly smaller than the outer diameter of the cylindrical member.

23. The method of claim 21 wherein rotation in one direction causes the inner diameter of the spring to increase, wherein the spring releases the cylindrical member.

24. The method of claim 21 wherein the cylindrical member is at least one of a tube, cord, conduit, duct, wire, cable, lead, fiber optic or fiber optic assembly.

25. The method of claim 21 further comprising providing a fastening mechanism to prevent the first and second sleeves from separating during rotation of the first sleeve relative to the second sleeve.

26. The method of claim 25 wherein providing the fastening mechanism further comprises forming the first sleeve with a slot integral in the first sleeve, forming the second sleeve with a hole integral in the second sleeve, and providing a pin for inserting through the hole and into the slot, thereby fastening the first and second sleeves.

27. The method of claim 21 wherein forming at least a portion of at least one of the first sleeve and the second sleeve comprises over-molding.

28. The method of claim 27 wherein the portion of the sleeve formed by over-molding is used to secure a portion of the spring.

* * * * *